United States Patent [19]

Emtage et al.

[11] 4,357,421
[45] Nov. 2, 1982

[54] SYNTHETIC GENE CODING FOR INFLUENZA HEMAGGLUTININ

[75] Inventors: John S. Emtage, High Wycombe; Norman H. Carey, Chinnor, both of England

[73] Assignee: G. D. Searle & Co., Skokie, Ill.

[21] Appl. No.: 132,960

[22] Filed: Mar. 24, 1980

[30] Foreign Application Priority Data

Apr. 2, 1979 [GB] United Kingdom ............... 7911487

[51] Int. Cl.$^3$ ............................................ C12N 15/00
[52] U.S. Cl. .................................... 435/68; 435/91; 435/172; 435/253; 435/317; 536/27; 260/112.5 R
[58] Field of Search ................ 435/172, 68, 317, 253, 435/91

[56] References Cited

PUBLICATIONS

C. Andrewes et al., "Viruses of Vertebrates," Third Edition, pp. 205–222, Bailliere Tindall, London, 1972.
"New Techniques in Biophysics and Cell Biology," vol. 3, R. H. Pain et al., eds., Chapter 4, pp. 125–145, by D. M. Glover, John Wiley & Sons, New York, 1976.
Chemical Abstracts, 94: 205256a, (1981).
A. J. Hay et al., Virology, 83, 337–355, (1977).
S. C. Inglis et al., Virology, 78, 522–536, (1971).
J. S. Emtage et al., Nature, vol. 283, No. 5743, 171–174, (Jan. 10, 1980).
A. G. Porter et al., Nature, vol. 282, No. 5738, 471–477, (Nov. 29, 1979).
J. S. Emtage et al., Nucleic Acids Research, vol. 6, No. 4, 1221–1239, (Apr. 1979).
D. McGeoch et al., Proc. Natl. Acad. Sci. USA, vol. 73, No. 9, 3045–3049, (Sep. 1976).
P. Palese et al., Proc. Natl. Acad. Sci. USA, vol. 73, No. 6, 2142–2146, (Jun. 1976).
J. J. Skehel et al., Nucleic Acids Research, vol. 5, No. 4, 1207–1219, (Apr. 1978).
A. E. Sippel, Eur. J. Biochem., 37, 31–40, (1973).
A. Efstratiadis et al., Cell, vol. 7, 279–288, (Feb. 1976).
R. Roychoudhury et al., Nucleic Acids Research, vol. 3, No. 4, 863–877, (Apr. 1976).
A. A. Gribnau et al., Archives of Biochemistry and Biophysics, 130, 48–52, (1969).
V. M. Vogt, Eur. J. Biochem., 33, 192–200, (1973).
M. Grunstein et al., Proc. Nat. Acad. Sci. USA, vol. 72, No. 10, 3961–3965, (Oct. 1975).
A. M. Maxam et al., Proc. Natl. Acad. Sci. USA, vol. 74, No. 2, 560–564, (Feb. 1977).

*Primary Examiner*—Sidney Marantz
*Attorney, Agent, or Firm*—James G. Passe; Albert Tockman

[57] ABSTRACT

A process for the production of a synthetic gene for an influenza haemagglutinin which comprises:
(a) subjecting isolated vRNA to the action of reverse transcriptase to produce a double-stranded RNA/DNA hybrid;
(b) digesting the RNA component of the hybrid;
(c) treating the residual DNA component of the hybrid to produce a double-stranded DNA molecule having one "hairpin" end; and
(d) treating the "hairpin" structure with a single-strand specific nuclease to produce a bimolecular double-stranded copy of the vRNA.

20 Claims, 6 Drawing Figures

3' UCGUUUUCGUCCCCAAUGUUUUACUUGUGAGUUUAGGACCAAAAGCGGGAACACCGUCAGU
5' AGCAAAAGCAGGGGUUACAAAAUGAACACUCAAAUCCUGGUUUUCGCCCUUGUGGCAGUCA
                                                    50

AGGGGUGUUUACGUCUGUUUUAAACAGAACCUGUAGUACGACAUAGUUUACCGUGGUUUCA
                            100
UCCCCACAAAUGCAGACAAAAUUUGUCUUGGACAUCAUGCUGUAUCAAAUGGCACCAAAGU

UUUGUGUGAGUGACUCUCUCCUCAUCUUCAACAGUUACGUUGCCUUUGUCACCUCGCCUGU
                            150
AAACACACUCACUGAGAGAGGAGUAGAAGUUGUCAAUGCAACGGAAACAGUGGAGCGGACA

BalI,HaeIII
UUGUAGGGGUUUUAAACGAGUUUUCCCUUUUCUUGGUGACUAGAACCGGUUACGCCUGACA
                    200
AACAUCCCCAAAAUUUGCUCAAAAGGGAAAAGAACCACUGAUCUUGGCCAAUGCGGACUGU

HpaII                      XbaI        PvuII
AUCCCUGGUAAUGGCCUGGUGGAGUUACGCUGGUUAAAGAUCUUAAAAGUCGACUAGAUUA
    250                                                      300
UAGGGACCAUUACCGGACCACCUCAAUGCGACCAAUUUCUAGAAUUUUCAGCUGAUCUAAU

TaqI                        AvaI, SmaI
UUAGCUCUCUGCUCUUCCUUUACUACAAACAAUGGGCCCCUUCAAACAAUUACUUCUCCGU
                                                  350
AAUCGAGAGACGAGAAGGAAAUGAUGUUUGUUACCCGGGGAAGUUUGUUAAUGAAGAGGCA

HinfI
AACGCUGUUUAGGAGUCUCCUAGUCCACCCUAACUGUUUCUUUGUUACCCUAAGUGUAUAU
                        400
UUGCGACAAAUCCUCAGAGGAUCAGGUGGGAUUGACAAAGAAACAAUGGGAUUCACAUAUA CACCUUAUUCCUGGUUGCCUUGUUGAUCACGUACAUCUUCUAGUCCCAGAAGUAAGAUACG
                        450
GUGGAAUAAGGACCAACGGAACAACUAGUGCAUGUAGAAGAUCAGGGUCUUCAUUCUAUGC Fig. 3 (Part 1 of 4)

```
UCUUUACCUCACCGAGGACAGUUUAUGUCUGUUACGAAGAAAGGGUGUUUACUGUUUUAGU
          500
AGAAAUGGAGUGGCUCCUGUCAAAUACAGACAAUGCUUCUUUCCCACAAAUGACAAAAUCA

Hinf I  AluI              Hinf I
AUGUUUUUGUGUUCCUCUCUUAGUCGAGACUAUCAGACCCCUUAGGUGGUAAGUCCUAGUU
550                                                    600
UACAAAAACACAAGGAGAGAAUCAGCUCUGAUAGUCUGGGGAAUCCACCAUUCAGGAUCAA GGUGGCUUGUCUGGUUUGAUAUACCCUCACCUUUAUUUGACUAUUGUCAGCCCUCAAGGUU
                            650
CCACCGAACAGACCAAACUAUAUGGGAGUGGAAAUAAACUGAUAACAGUCGGGAGUUCCAA Hinf I                 Bal I,Hae III  Hoa II
UAUAGUAGUUAGAAAACACGGCUCAGGUCCUUGUGCUGGCGUCUAUUUACCGGUCAGGCCU
                         700
AUAUCAUCAAUCUUUUGUGCCGAGUCCAGGAACACGACCGCAGAUAAAUGGCCAGUCCGGA BamHI
GCCUAACUAAAAGUAACCAACUAGAACCUAGGGUUACUAUGUCAAUGAAAAUCAAAGUUAC
                  750
CGGAUUGAUUUUCAUUGGUUGAUCUUGGAUCCCAAUGAUACAGUUACUUUUAGUUUCAAUG BamH I
CCCGAAAGUAUCGAGGUUUAGCACGGUCGAAGAACUCCCCUUUCAGGUACCCCUAGGUCUC
    800                                                  850
GGGCUUUCAUAGCUCCAAAUCGUGCCAGCUUCUUGAGGGGAAAGUCCAUGGGGAUCCAGAG GCUACACGUCCAACUACGAUUAACGCUUCCCCUUACGAUGGUGUCACCUCCCUGAUAUUGU
                                                 900
CGAUGUGCAGGUUGAUGCUAAUUGCGAAGGGGAAUGCUACCACAGUGGAGGGACUAUAACA UCGUCUAACGGAAAAGUUUUGUAUUUAUCGUCUCGUCAACCGUUUACGGGUUCUAUACAUU
                            950
AGCAGAUUGCCUUUUCAAAACAUAAAUAGCAGAGCAGUUGGCAAAUGCCCAAGAUAUGUAA
```

Fig. 3 (Part 2 of 4)

UUGUCCUUUCAAAUAAUAACCGUUGACCCUACUUCUUGCAAGGGCUUGGAAGGUUUUUUUC
                              1000
AACAGGAAAGUUUAUUAUUGGCAACUGGGAUGAAGAACGUUCCCGAACCUUCCAAAAAAG

HaeIII   HhaI
CCUUUUUUCUCCGGACAAACCGCGAUAUCGUCCCAAAUAACUUUUACCAACCCUUCCAGAC
                    1,050
GGAAAAAAGAGGCCUGUUUGGCGCUAUAGCAGGGUUUAUUGAAAAUGGUUGGGAAGGUCUG

SalI,HincII                      PstI
 CAGCUGCCCACCAUGCCAAAGUCCGUAGUCUUACGUGUUCCUCUUCCUUGACGUCGUCUGA
1,100                               1,150
 GUCGACGGGUGGUACGGUUUCAGGCAUCAGAAUGCACAAGGAGAAGGAACUGCAGCAGACU HpaII      HinfI
UGUUUUCGUGGGUUAGCCGUUAACUAGUCUAUUGGCCUUUCAAUUUAUCUGAGUAACUCUU
                              1,200
ACAAAAGCACCCAAUCGGCAAUUGAUCAGAUAACCGGAAAGUUAAAUAGACUCAUUGAGAA AluI     EcoRI
UUGGUUGGUCGUUAAACUCGAUUAUCUAUUACUUAAGUGACUUCACCUUUUCGUCUAACCG
                    1,250
AACCAACCAGCAAUUUGAGCUAAUAGAUAAUGAAUUCACUGAAGUGGAAAAGCAGAUUGGC UUAAAUUAAUUGACCUGGUUUCUGAAGUAGUGUCUUCAUACCAGAAUGUUACGACUUGAAG
                    1,300
AAUUUAAUUAACUGGACCAAAGACUUCAUCACAGAAGUAUGGUCUUACAAUGCUGAACUUC HinfI      AluI
AACACCGUUACCUUUUGGUCGUGUGAUAACUAAACCGACUAAGUCUCUACUUGUUCGACAU
 1 350                                 1,400
UUGUGGCAAUGGAAAACCAGCACACUAUUGAUUUGGCUGAUUCAGAGAUGAACAAGCUGUA ACUCGCUCACUCCUUUGUUAAUUCCCUUUUACGACUUCUCCUACCGUGACCAACGAAACUU
                              1,450
UGAGCGAGUGAGGAAACAAUUAAGGGAAAAUGCUGAAGAGGAUGGCACUGGUUGCUUUGAA Fig. 3 (Part 3 of 4)

UAAAAAGUAUUUACACUGCUACUAACAUACCGAUCAUAUUCCUUGUUAUGAAUACUAGUGU
1,500
AUUUUUCAUAAAUGUGACGAUGAUUGUAUGGCUAGUAUAAGGAACAAUACUUAUGAUCACA

CGUUUAUGUCUCUUCUUCGCUACGUUUUAUCUUAUGUUUAACUGGGUCAGUUUAACUCAUC
1,550
GCAAAUACAGAGAAGAAGCGAUGCAAAAUAGAAUACAAAUUGAUCCAGUCAAAUUGAGUAG

AluI
ACCGAUGUUUCUACACUAUGAAACCAAAUCGAAGCCCCGUAGUACGAAAAACGAAGAACG
1,600
UGGCUACAAAGAUGUGAUACUUUGGUUUAGCUUCGGGGCAUCAUGCUUUUUGCUUCUUGC

HaeIII
GUAACGUCACCCGGAACAAAAGUAUACACACUUCUUGCCUUUGUACGCCACGUGAUAAACA
1,650                            1,700
CAUUGCAGUGGGCCUUGUUUUCAUAUGUGUGAAGAACGGAAACAUGCGGUGCACUAUUUGU

UAUAUUCAAACCUUUUUUUGUGGGAACAAAGAUGA 5'    vRNA

AUAUAAGUUUGGAAAAAAACACCCUUGUUUCUACU 3'    cRNA

Fig.3 (Part 4 of 4)

AGCAAAAGCAGGGGTTACAAAATG.AAC.ACT.CAA.ATC.
                        Met Asn Thr Gln Ile

CTG.GTT.TTC.GCC.CTT.GTG.GCA.GTC.ATC.CCC.
Leu Val Phe Ala Leu Val Ala Val Ile Pro

ACA.AAT.GCA.GAC.AAA.ATT.TGT.CTT.GGA.CAT.
Thr Asn Ala Asp Lys Ile Cys Leu Gly His

CAT.
His

Fig. 5A

AAA.AAA.AGG.GAA.AAA.AGA.GGC.CTG.TTT.GGC.
Lys Lys Arg Glu Lys Arg Gly Leu Phe Gly

GCT.ATA.GCA.GGG.TTT.ATT.GAA.AAT.GGT.TGG.
Ala Ile Ala Gly Phe Ile Glu Asn Gly Trp

GAA.GGT.CTG.GTC.GAC.GGG.TGG.TAC.GGT.TTC
Glu Gly Leu Val Asp Gly Trp Tyr Gly Phe

AGG.CAT.CAG.AAT
Arg His Gln Asn

Fig. 5B

SYNTHETIC GENE CODING FOR INFLUENZA HEMAGGLUTININ

This invention relates to synthetic influenza genes.

Influenza viruses are a family of negative-stranded RNA viruses, (Andrewes, C., et al., (1972), Viruses of Vertebrates, 3rd. Edn., Bailliere Tindall, London, 205–222), that is, they contain an RNA genome which lacks infectivity and must be replicated during infection to produce both viral messenger RNA (m RNA) and templates for further viral RNA (v RNA), (Hay, A. J., et al., (1977), Virology, 83, 337–355). DNA is not known to play a part in the transcription of vRNA to mRNA and the subsequent protein synthesis.

The influenza A virus, for example, comprises a segmented genome consisting of eight single-stranded RNA segments, (Mc. Geogh, D., et al., (1976), Proc. Natl. Acad. Sci. USA, 73, 3045–3049), and it is known that the major influenza antigenic determinant, the haemagglutinin, is produced by RNA 4 in viruses, such as Fowl Plague Virus (FPV) and Influenza A/Victoria/75 (A/Victoria), (Inglis, S. C., et al., (1977), Virology, 78, 522–536; Palese, P., et al., (1976), Proc. Natl. Acad. Sci. USA, 73, 2142–2146).

One object of the present invention is the production of a synthetic influenza haemagglutinin gene which is a double-stranded complementary DNA (cDNA) copy of a given specific influenza vRNA and which is capable of insertion into a bacterial plasmid engineered to ensure translation through the inserted DNA and expression of a polypeptide which will act as an influenza vaccine.

It has been found that isolated vRNA, possibly suitably modified may be subjected to reverse transcription in the presence of a suitable primer to produce a single-stranded cDNA copy which in turn may be treated with reverse transcriptase to produce a synthetic gene, which is an exact double-stranded cDNA copy of the original vRNA. It is to be understood that the present invention is applicable to the production of synthetic genes derived from any influenza vRNA.

One aspect of the present invention relates to a process for the production of a synthetic gene for an influenza haemagglutinin which comprises:

(a) subjecting isolated vRNA to the action of reverse transcriptase to produce a double-stranded RNA/DNA hybrid;

(b) digesting the RNA component of the hybrid;

(c) treating the residual DNA component of the hybrid to produce a double-stranded DNA molecule having one "hairpin" end; and (d) treating the "hairpin" structure with a single strand specific nuclease to produce a bimolecular double-stranded copy of the vRNA.

Step (a) may involve:

(i) adding to the reaction mixture a short, for example at least 8 member, deoxynucleotide sequence synthesised so as to be complementary to a known sequence at the 3' terminal sequence of the vRNA;

(ii) extending the 3' terminus of the vRNA using a homoribonucleotide sequence, for example polyriboadenylic acid added with the aid of ATP:RNA adenyltransferase (EC 2.7.7.19) (poly A polymerase), and adding to the reverse transcription reaction a homo-oligodeoxynucleotide complementary to this 3' extension; or (iii) utilizing one or more pre-existing structural features of the vRNA which result in self-priming.

Regarding (iii), in the case of A/Victoria gene 4, for example, the primary structure of the 3' end of the vRNA is such that a relatively stable "loop" structure may exist and act as an initiation site for reverse transcription in the absence of an exogenous primer.

A suitable specific nuclease for step (d) is S1 nuclease (E.C. 3.1.4.-).

The process according to the present invention may be represented schematically as illustrated in FIG. 1 of the accompanying drawings.

The first stage of the present process, reverse transcription of the vRNA, may be conducted in the presence of a suitable added primer. The 3' terminal sequence of influenza vRNA is known, (Skehel, J. J., et al., (1978), Nucleic Acids Res., 5, 1207–1219), and is as follows:

5'-----CCUGCUUUUGCU 3' and so a suitable primer would be, for example;

5' AGCAAAAGCAGG 3' although a shorter primer of, say, from 8 to 10 of the above nucleotides may be used.

Alternatively, reverse transcription may be carried out in the presence of a primer specific to a known nucleotide sequence added to the 3' end of the vRNA. For example, the vRNA may be treated with poly A polymerase in the presence of magnesium and/or manganous ions to produce a poly A tail at the 3' end and reverse transcription is carried out in the presence of oligo(dT) as primer and thereafter the process continued as described above.

The embodiment of the present process utilising an initial polyadenylation stage may be represented schematically as illustrated in FIG. 2 of the accompanying drawings.

In order to improve the efficiency of the polyadenylation reaction, it is generally carried out in the presence of sodium chloride, (Sippel, A. E., (1973), Eur. J. Biochem., 37, 31–40).

Digestion of the RNA component of the RNA/DNA hybrid may be effected using an alkali, e.g. sodium hydroxide, (Efstratiadis, A., et al., (1976), Cell, 7, 279–288), or using ribonuclease, (loc cit).

The conversion of the single-stranded cDNA into the double-stranded cDNA "hairpin" structure may be carried out using reverse transcriptase or another DNA polymerase, for example E. coli DNA polymerase E.C. 2.7.7.7.

The product of the present process is a double-stranded cDNA copy of the specific vRNA used. Such double-stranded cDNA replicas of vRNA are novel and one aspect of the present invention is directed accordingly.

The synthetic genes according to the present invention may be cloned in bacterial plasmids suitably designed to ensure, firstly, insertion of the gene at a predetermined site and, secondly, that the insertion site is near to a strong bacterial promoter so that transcription of the gene is initiated at the promoter and proceeds through the inserted gene. Such bacterial plasmids are known, for example the so-called "pWT series" disclosed in G.B. patent application No. 79 19245.

Various methods are known for the insertion of DNA fragments into plasmids.

One method of insertion depends upon the modification of the synthetic gene to provide on the gene terminal sites for a particular restriction enzyme relevant to the restriction site on the plasmid into which the gene is to be inserted. Thus, where the gene is to be inserted into a plasmid having a Hind III restriction site suitably positioned near a strong bacterial promoter, Hind III linkers (Collaborative Research, Waltham, Mass., USA) are ligated to the ends of the gene, which is then treated with the Hind III restriction enzyme (EC 3.1.23.21) producing the so-called Hind III "sticky ends" which allow the modified gene to be easily cloned in a Hind III plasmid vector.

Another method which may in some circumstances be used depends upon the use of a suitably designed plasmid having two relevant insertion sites corresponding to naturally occurring restriction sites on the synthetic gene. Thus, the synthetic A/Victoria gene which may be produced by the present process has a Hind III site near one end and a Bam HI site near the other end. Using a plasmid vector having a Hind III site near to a strong promoter and a Bam HI site downstream from the Hind III site, both the gene and the plasmid may be digested with Hind III and Bam HI (EC 3.1.23.-) and the digestion products ligated to form a reconstituted plasmid having the gene inserted between the Hind III and the Bam HI sites and subject to the promoter near the Hind III site.

The so-called "tailing" method, (Roychoudhury, R., et al., (1976), Nucleic Acids Research, 3, 863–877), may also be used. Thus, a suitable plasmid is restricted at a site near to a strong promoter and the thus-obtained linear DNA is tailed, for example using terminal deoxynucleotidyl transferase (EC 2.7.7.31) (terminal transferase) and dGTP to produce G tails on the linear DNA. The gene is provided with complementary tailing, for example by treatment with terminal transferase and dCTP to produce C tails. The products are mixed and annealed to form a reconstituted plasmid having the gene inserted at the original restriction site of the plasmid and subject to the promoter near that site.

Appropriate plasmids containing the present synthetic influenza genes may be used to transform transformable cells, in particular $E.\ coli$ cells, in known manner, (Glover, D., New Techniques in Biophysics and Cell Biology, Vol. 8., (Eds. Pain, R. H., and Smith, B. J.), 125–145, (Wiley, New York, 1976), for example by exposure of cells treated with calcium chloride to the plasmid DNA preparations. Such transformed cells grown in appropriate culture media express the inserted gene, the product of which is a polypeptide dictated by the nucleotide sequence of the cloned synthetic gene, under the influence of the adjacent bacterial promoter of the parent plasmid. The polypeptide may be harvested in known manner, for example by centrifuging the cells and lysing them by exposure to sonic oscillation or detergents. The polypeptide may be purified from bacterial proteins in the lysate by known methods of protein purification. This polypeptide, which contains the polypeptide sequence of the influenza haemagglutinin corresponding to that of the virus from which the gene was copied, is an antigen which is capable of raising antibodies in injected animals in a manner similar to that of the haemagglutinin purified directly from the virus. The antigen may be administered for vaccine purposes by the known procedures, e.g. by injection subcutaneously, intramuscularly or intravenously, in the presence or absence of appropriate adjuvants.

BRIEF DESCRIPTION OF THE DRAWINGS

In the drawings:

FIG. 3 is the FPV haemagglutinin gene structure in terms of RNA;

FIGS. 5A and 5B are a representation of the nucleotide sequences of the coding strand of the two regions (a) and (b) in FIG. 4, together with the amino acid sequence predicted by this sequence.

The present invention is further illustrated by the following:

PREPARATION OF SYNTHETIC FPV GENE

Isolation of the virus RNA

Figure 1:
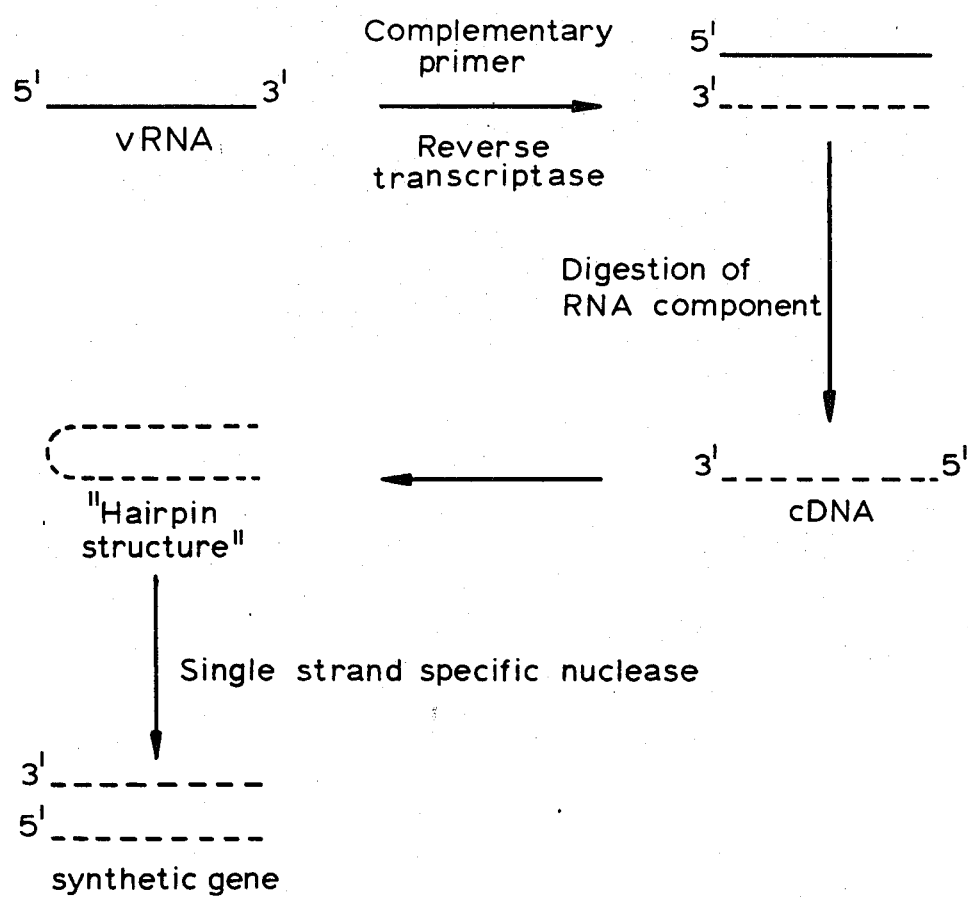
FIG. 1 is a schematic representation of the process of the present invention.
Figure 2:
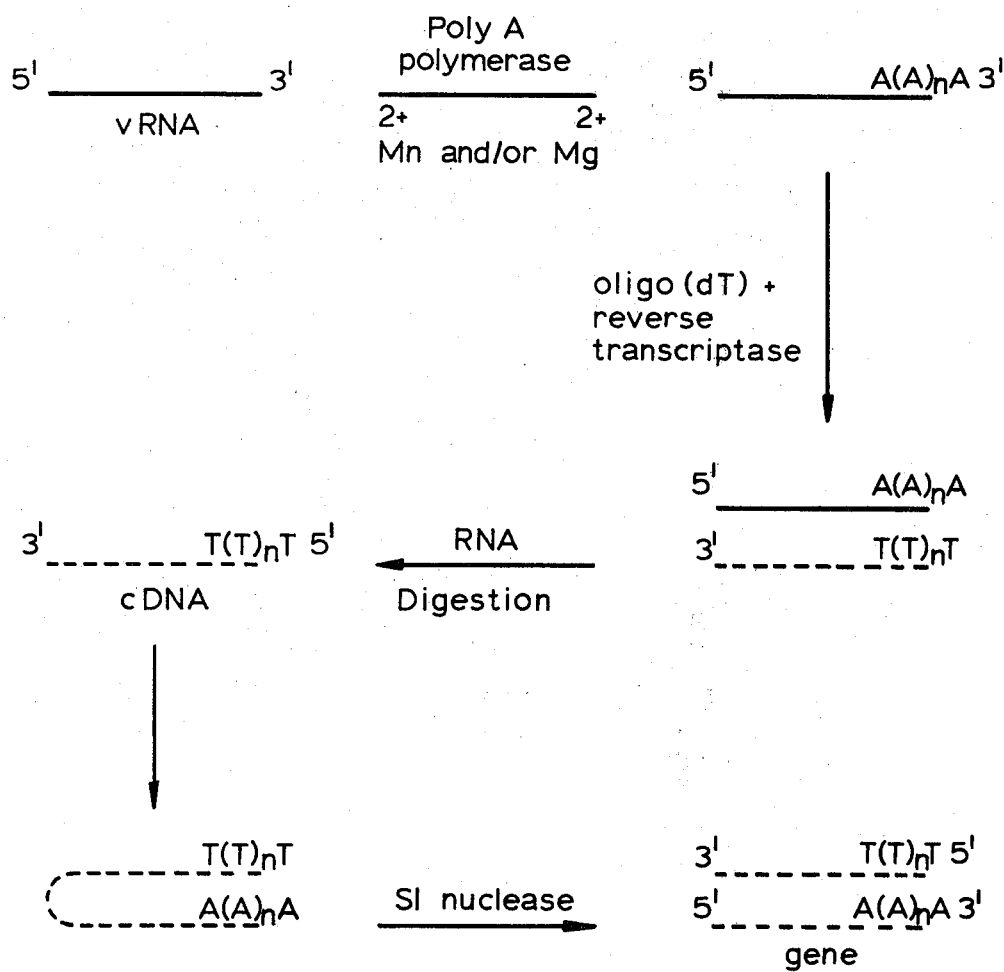
FIG. 2 is a schematic representation of the present process utilizing an initial polyadenylation stage.

The Rostock strain of FPV was grown in 10-day-old embryonated hens' eggs at 37° C. for from 18 to 30 hours. The allantoic fluid was collected, centrifuged at 2,000 rpm for 10 minutes to remove red cells and other cellular debris. Virus was then harvested from the resulting supernatant by centrifugation at 18,000 rpm for 90 minutes. Virus pellets were resuspended in NTE (i.e. $10^{-1}$ M NaCl, $10^{-2}$ M Tris-HCl pH 7.5, $10^{-3}$ M ethylene diamine tetra acetic acid (EDTA)) by gentle homogenisation, spun at 5,000 rpm for 4 minutes to remove aggregated yolk protein and the supernatant removed. The virus was finally purified on a 15%–60% w/v linear sucrose gradient in NTE by banding to equilibrium at 24,000 rpm for 3 hours at 4° C. The virus band, appearing about ⅓ from the bottom of the tube, was removed by suction, diluted to twice its volume with NTE and pelleted at 25,000 rpm for 40 minutes at 4° C.

The pellet of virus was resuspended in 5 ml NTE, sodium dodecylsulphate (SDS) added to 0.2% w/v and the mixture extracted with phenol and chloroform. The final aqueous phase was made to $2 \times 10^{-1}$ M with NaCl and RNA precipitated by the addition of 2.5 volumes of ethanol. Ethanol precipitates were pelleted (11,000 rmp, 20 minutes), washed with ethanol, dried in vacuo and dissolved in TE buffer (i.e. $10^{-2}$ M Tris-HCl pH 7.5, $10^{-3}$ M EDTA). RNA was quantitated assuming that 1 mg/ml = 20 $A_{260}$.

Polyadenylation vRNA was polyadenylated at 37° C. The reaction mixture contained $5 \times 10^{-2}$ mM Tris-HCl pH 8, $10^{-2}$ M MgCl$_2$, $10^{-3}$ M MnCl$_2$, 50 μg/ml purified ovalbumin, $10^{-4}$ M $^3$H ATP, $2 \times 10^{-1}$ M NaCl, 50 μg/ml viral RNA and 1/10 volume of poly (A) polymerase. Incubation was terminated by the addition of SDS to 0.2% w/v and EDTA to $2 \times 10^{-2}$ M. The product was extracted with phenol and chloroform as described above and the final aqueous phase precipitated by the addition of an equal volume of 4 M NH$_4$ Acetate and then 2.5 volumes of ethanol.

Synthesis of single-stranded cDNA

DNA complementary to the polyadenylated vRNA was synthesised in a mixture containing $5 \times 10^{-2}$ M Tris-HCl pH 8.3, 6 mM Mg Cl$_2$, $2\times 10^{-4}$ M dGTP, $2\times 10^{-4}$ M dATP, $2\times 10^{-4}$ M TTP, $5\times 10^{-5}$ M dCTP ($^{32}$P or $^3$H as indicated), $5\times 10^{-3}$ M DTT, 0.01% v/v Triton (Registered Trade Mark) X-100, 50 µg/ml actinomycin D, $4\times 10^{-2}$ M KCl, 10 units/ml rat liver ribonuclease inhibitor, (Gribrau, et al., (1969), Arch. Biochem. Biophys., 130, 48–52), 5 µg/ml oligo (dT)$_{12-18}$, 20 µg/ml adenylated RNA and 60 units/ml reverse transcriptase. After incubation at 37° C. for 90 minutes, the mixture was made 0.2% w/v with SDS, $2\times 10^{-2}$ M with EDTA and a 10 µl aliquot removed for TCA precipitation. To the remainder was added an equal volume of 4 M NH$_4$Acetate and the cDNA precipitated by the addition of 2.5 volumes of ethanol. cDNA was recovered by centrifugation, dissolved in 100 µl H$_2$O and then made to $3\times 10^{-1}$ M with NaOH. After overnight incubation at 37° C., the sample was neutralised with acetic acid and chromatographed on a $50\times 0.7$ cm column of Sephadex (Registered Trade Mark) G-150 equilibrated in $5\times 10^{-2}$ M NaCl/0.1% w/v SDS. DNA eluting in the void volume was pooled and concentrated by ethanol precipitation.

Enzymatic synthesis of double-stranded cDNA

Double-stranded cDNA was synthesised from single-stranded cDNA in an incubation containing $5\times 10^{-2}$ M Tris pH 8.3, $2\times 10^{-2}$ M DTT, $10^{-2}$ M MgCl$_2$, $4\times 10^{-4}$ M dGTP, $4\times 10^{-4}$ M dATP, $4\times 10^{-4}$ M TTP, $1\times 10^{-4}$ M dCTP, 2.5-10 µg/ml cDNA and 400 units/ml reverse transcriptase. Incubation was at 45° C. The reaction mixture was then made $2\times 10^{-2}$ M with EDTA, 0.2% w/v with SDS, extracted with phenol and chloroform and placed on a Sephadex G-50 column ($20\times 0.7$ cm) equilibrated in $5\times 10^{-2}$ M NaCl and 0.1% w/v SDS. The excluded fractions were pooled.

S1 nuclease treatment

The products of the reverse transcriptase reactions were treated with S1 nuclease (E.C. 3.1.4.-) purified from α-amylase by heat treatment, ammonium sulphate precipitation and DEAE-cellulose chromatography, (Vogt, V. M., (1973), Eur. J. Biochem., 33, 192–200).

The reaction mixtures (100–200 µl) contained $1.5\times 10^{-1}$ M NaCl, $2.5\times 10^{-2}$ M sodium acetate pH 4.6, $1\times 10^{-3}$ M ZnSO$_4$, DNA and 2.5-5 units of S1 nuclease and incubation was at 37° C. for 30 minutes.

The double-stranded cDNA copy of the gene produced by the above method was inserted into a known bacterial plasmid by the above-described linker method. Clones containing the haemagglutinin gene were identified by hybridisation to radioactive gene 4-RNA (Grunstein et al., (1975), Proc. Natl. Acad. Sci. USA, 72, 3961–3965). Sequencing was by known methods, (Maxam, A., et al., (1977), Proc. Natl. Acad. Sci. USA, 74, 560–564).

For purposes of illustration, the FPV haemagglutinin gene structure, in terms of RNA, is represented in FIG. 3 of the accompanying drawings.

Figure 4:
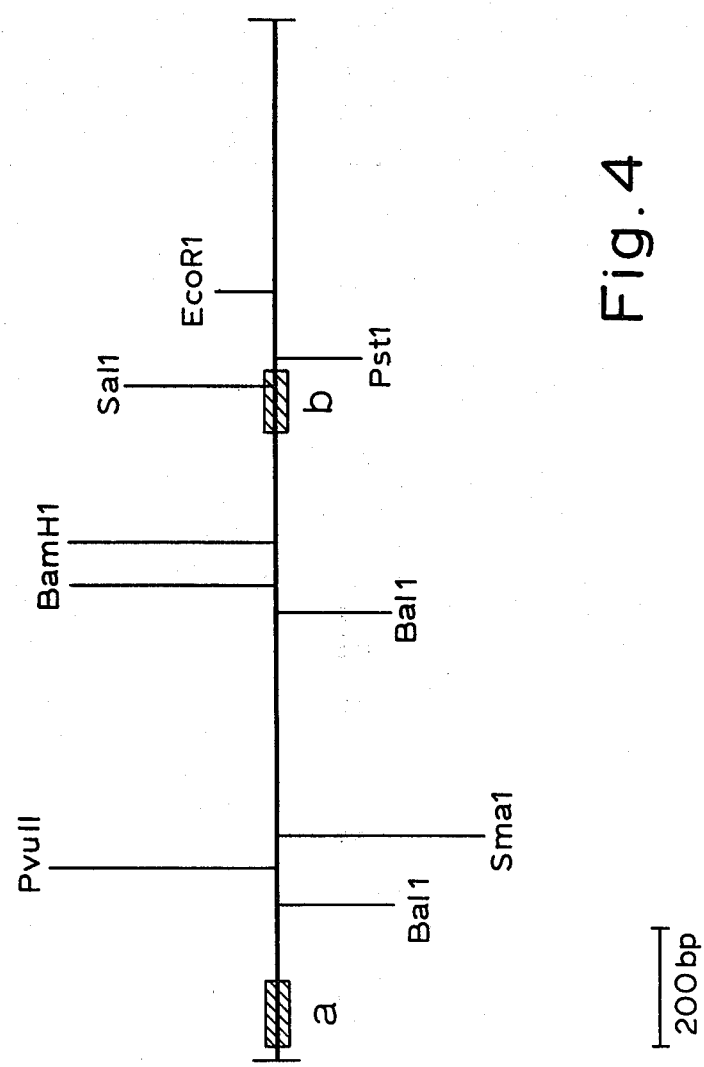
FIG. 4 is an alternate representation of the structure in FIG. 3.

The structure is represented in an alternative form in FIG. 4 of the accompanying drawings.

To more fully illustrate the gene structure, the nucleotide sequences of the coding strand of the two regions (a) and (b) in FIG. 4, together with the amino acid sequence predicted by this sequence, are represented in FIG. 5 of the accompanying drawings.

SYNTHESIS OF SYNTHETIC A/VICTORIA GENE

Isolation of virus RNA

Commercially available Influenza A/Victoria/75, obtained from Evans Medical Co., Liverpool, England, was used.

To 10 ml virus suspension (at 4 mg protein/ml) was added an equal volume of 0.4% w/v SDS, $4\times 10^{-2}$ M EDTA. The mixture was extracted with 20 ml of phenol and 20 ml of chloroform. After phase separation, the organic layer was re-extracted with 5 ml NTE. The two aqueous phases (plus interfaces) were pooled and extracted twice with equal volumes of chloroform. RNA was finally precipitated by the addition of 2½ volumes of ethanol.

Ethanol precipitates were pelleted, dissolved in 1 ml TE and spun (10,000 rpm, 10 minutes) to remove insoluble material. vRNA was reprecipitated by the addition of 3 volumes of 4 M NaCl. After standing at $-20°$ C. for 16 hours, the RNA was again pelleted, washed with 70% ethanol, dried and dissolved in TE.

Polyadenylation, synthesis of single-stranded cDNA, enzymatic synthesis of double-stranded cDNA and S1 nuclease treatment could be carried out as described above.

Synthesis of cDNA by self-priming of HA gene $^{32}$P-labelled cDNA was produced as described above, except that the RNA template (total vRNA) was not polyadenylated and that no oligo (dT) primer was added. Under these conditions, only gene 4 is efficiently copied by reverse transcriptase to give a near full-length transcript. Double-stranded DNA was synthesised from this cDNA and treated with S1 nuclease as described above.

What is claimed is:

1. A process for the production of a synthetic gene for an influenza haemagglutinin comprising:
   (a) subjecting isolated influenza vRNA to the action of reverse transcriptase to produce a double-stranded RNA/DNA hybrid;
   (b) digesting the RNA component of the hybrid;
   (c) treating the residual DNA component of the hybrid to produce a double-stranded DNA molecule having one "hairpin" end; and
   (d) treating the "hairpin" structure with a single strand specific nuclease to produce a bimolecular double-stranded copy of the vRNA.

2. A process according to claim 1 wherein, in (a), a primer is used which is a deoxynucleotide sequence complementary to a known sequence in the 3' terminal sequence of the vRNA.

3. A process according to claim 1 wherein, in (a), the vRNA is treated with ATP:RNA adenyltransferase in the presence of Mg$^{2+}$ and/or Mn$^{2+}$ to produce a 3' polyriboadenylic acid extension of the vRNA and reverse transcription is carried out in the presence of a primer which is a homo-oligodeoxynucleotide complementary to the 3' extension.

4. A process according to claim 1 wherein, in (a), a pre-existing 3' terminal nucleotide sequence present in the vRNA is used as a primer resulting in self-priming in the reverse transcription reaction.

5. A process according to claim 1 wherein, in (b), the RNA component of the RNA/DNA hybrid is digested with an alkali or ribonuclease.

6. A process according to claim 1 wherein, in (c), the single-stranded DNA is converted into a double-stranded DNA "hairpin" structure with reverse transcriptase or a DNA polymerase.

7. A process according to claim 1 wherein, in (d), the single-strand specific nuclease is S1 nuclease.

8. A synthetic gene for an influenza haemagglutinin produced by the process according to claim 1.

9. A plasmid vector comprising, inserted therein, a synthetic gene according to claim 8, the plasmid reading in the correct phase for the expression of the gene and having a bacterial promoter upstream thereof.

10. A process for the transformation of a transformable cell comprising inserting therein a plasmid vector according to claim 9.

11. A process according to claim 10 wherein clones containing the haemagglutinin gene are identified and separated.

12. A cell comprising a plasmid vector produced by a process according to claim 9.

13. A cell according to claim 12 which is an *E. Coli* cell.

14. A process for the production of a protein by the expression of a synthetic gene for an influenza haemagglutinin comprising culturing a cell according to claim 12.

15. A plasmid vector according to claim 9 wherein the plasmid is of the pWT series.

16. A process for the transformation of a transformable cell comprising inserting therein a plasmid vector according to claim 15.

17. A process according to claim 16 wherein clones containing the haemagglutinin gene are identified and separated.

18. A cell comprising a plasmid vector produced by a process according to claim 15.

19. A cell according to claim 18 which is an *E. Coli* cell.

20. A process for the production of a protein by the expression of a synthetic gene for an influenza haemagglutinin comprising culturing a cell according to claim 16.

* * * * *